United States Patent
Dunn

(10) Patent No.: US 6,263,887 B1
(45) Date of Patent: Jul. 24, 2001

(54) LIQUID WASTE DISPOSAL AND CANISTER FLUSHING SYSTEM AND METHOD

(75) Inventor: James L. Dunn, Topeka, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 0 days.

(21) Appl. No.: 09/483,295

(22) Filed: Jan. 14, 2000

(51) Int. Cl.$^7$ ........................................................ B08B 9/28
(52) U.S. Cl. ................... 134/22.18; 134/23; 134/140; 134/152; 134/153; 134/159; 134/169 R; 422/303
(58) Field of Search ................... 134/22.18, 23, 134/62, 140, 145, 152, 153, 159, 166 R, 169 R; 422/303

(56) References Cited

U.S. PATENT DOCUMENTS

| | | |
|---|---|---|
| 1,653,242 * | 12/1927 | Underwood ..................... 134/145 X |
| 1,693,885 | 12/1928 | Butterworte . |
| 1,827,085 | 10/1931 | Huff . |
| 2,370,775 | 3/1945 | Capita . |
| 2,641,270 | 6/1953 | Allen . |
| 2,896,643 | 7/1959 | Ottoson . |
| 3,078,861 | 2/1963 | Miller . |
| 3,122,151 | 2/1964 | Chambers . |
| 3,603,328 | 9/1971 | Fenn . |
| 3,615,822 * | 10/1971 | Molinari ............................. 134/23 |
| 3,645,283 | 2/1972 | Cassells . |
| 3,780,757 | 12/1973 | Jordan . |
| 3,791,394 | 2/1974 | Hammelmann . |
| 3,897,599 | 8/1975 | Artzer . |
| 3,916,924 | 11/1975 | Mc Gowan . |
| 3,989,046 | 11/1976 | Pannier, Jr. et al. . |
| 4,058,412 | 11/1977 | Knapp et al. . |
| 4,084,723 | 4/1978 | Parker . |
| 4,306,557 | 12/1981 | North . |
| 4,430,084 | 2/1984 | Deaton . |
| 4,455,140 | 6/1984 | Joslin . |
| 4,540,413 | 9/1985 | Russo . |
| 4,809,860 | 3/1989 | Allen . |
| 4,863,446 | 9/1989 | Parker . |
| 4,905,325 | 3/1990 | Colditz . |
| 4,957,491 | 9/1990 | Parker . |
| 4,961,440 | 10/1990 | Wright . |
| 4,972,976 | 11/1990 | Romero . |
| 5,011,470 | 4/1991 | Kurtz et al. . |
| 5,024,613 | 6/1991 | Vasconcellos et al. . |
| 5,186,195 | 2/1993 | Wall . |

(List continued on next page.)

Primary Examiner—Philip R. Coe
(74) Attorney, Agent, or Firm—Piper Marbury Rudnick & Wolfe

(57) ABSTRACT

A liquid waste disposal and canister flushing system and method for a medical canister including a lid with at least first and second ports features a cabinet with an opening and a sink with a drain positioned therein. A removable lid covers the cabinet opening. A canister holder in the form of a ring or bucket is positioned within the chamber defined between the sink and cabinet opening. The canister holder is supported by a rod that is rotatably positioned in the cabinet. The rod is also connected to an electric motor or lever so that the canister holder, and therefore the canister positioned therein, may be rotated between an initial position and a drainage position. The canister is secured within the canister holder and tubing, which is in communication with a source of pressurized and diluted cleaning solution, is connected to the first canister port. The canister is rotated into the drainage position and the pressurized and diluted cleaning solution source is activated to flush the canister contents out of the second lid port and into the sink and drain. The first canister port may optionally feature a nozzle oriented at an angle so that a swirling action is induced upon the pressurized liquid entering the canister to assist in the flushing of residue from the canister.

20 Claims, 8 Drawing Sheets

U.S. PATENT DOCUMENTS

| | | |
|---|---|---|
| 5,222,530 | 6/1993 | Baker et al. . |
| 5,273,083 | 12/1993 | Burrows . |
| 5,460,193 | 10/1995 | Levallois et al. . |
| 5,620,428 | 4/1997 | Hand . |
| 5,637,103 | 6/1997 | Kerwin et al. . |
| 5,683,371 | 11/1997 | Hand . |
| 5,688,255 | 11/1997 | Hand . |
| 5,776,260 | 7/1998 | Dunn et al. . |
| 5,807,359 | 9/1998 | Bemis et al. . |
| 5,871,476 | 2/1999 | Hand . |
| 5,901,717 | 5/1999 | Dunn et al. . |
| 5,931,822 | 8/1999 | Bemis et al. . |
| 5,975,096 | 11/1999 | Dunn et al. . |

\* cited by examiner

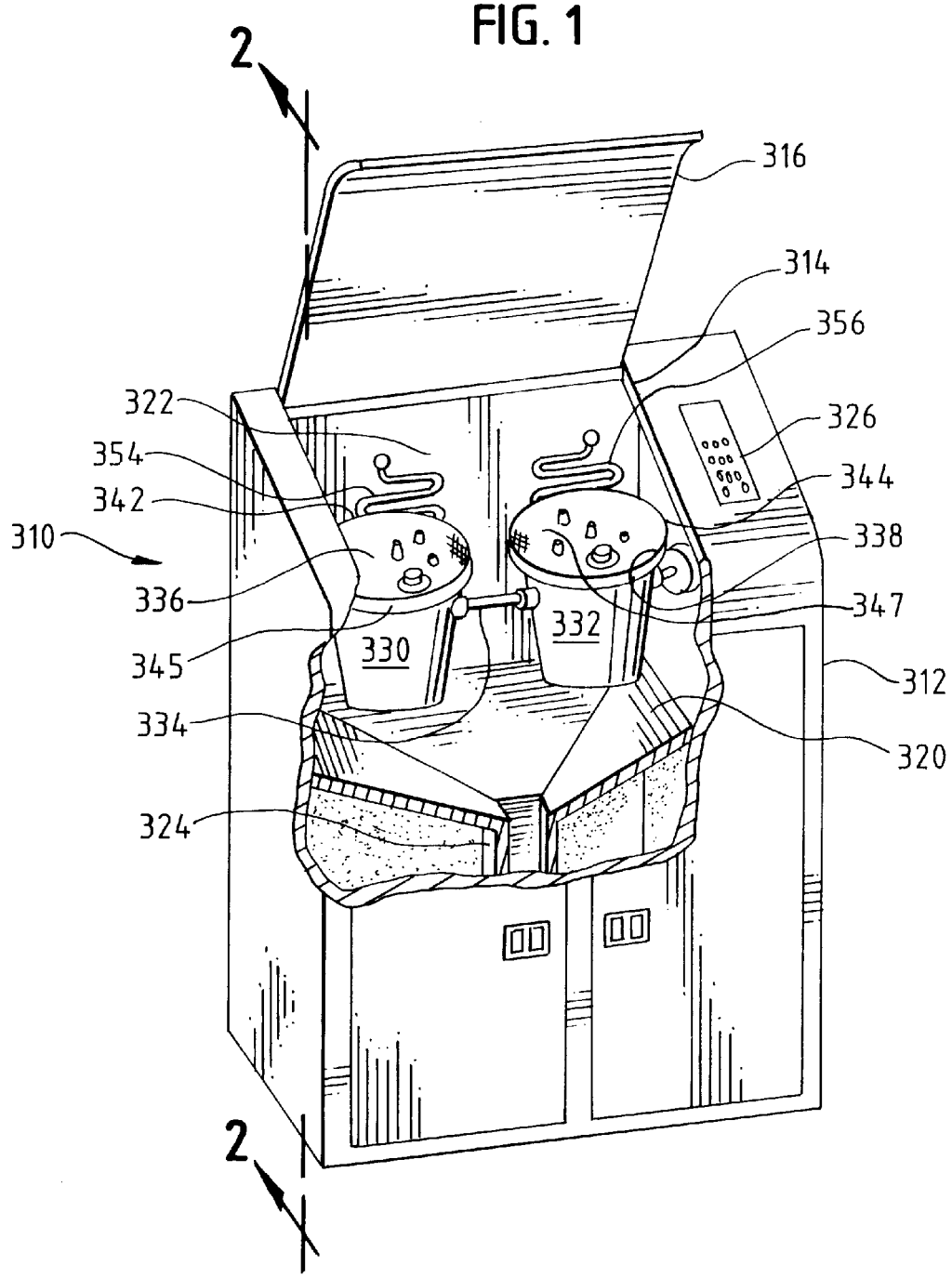

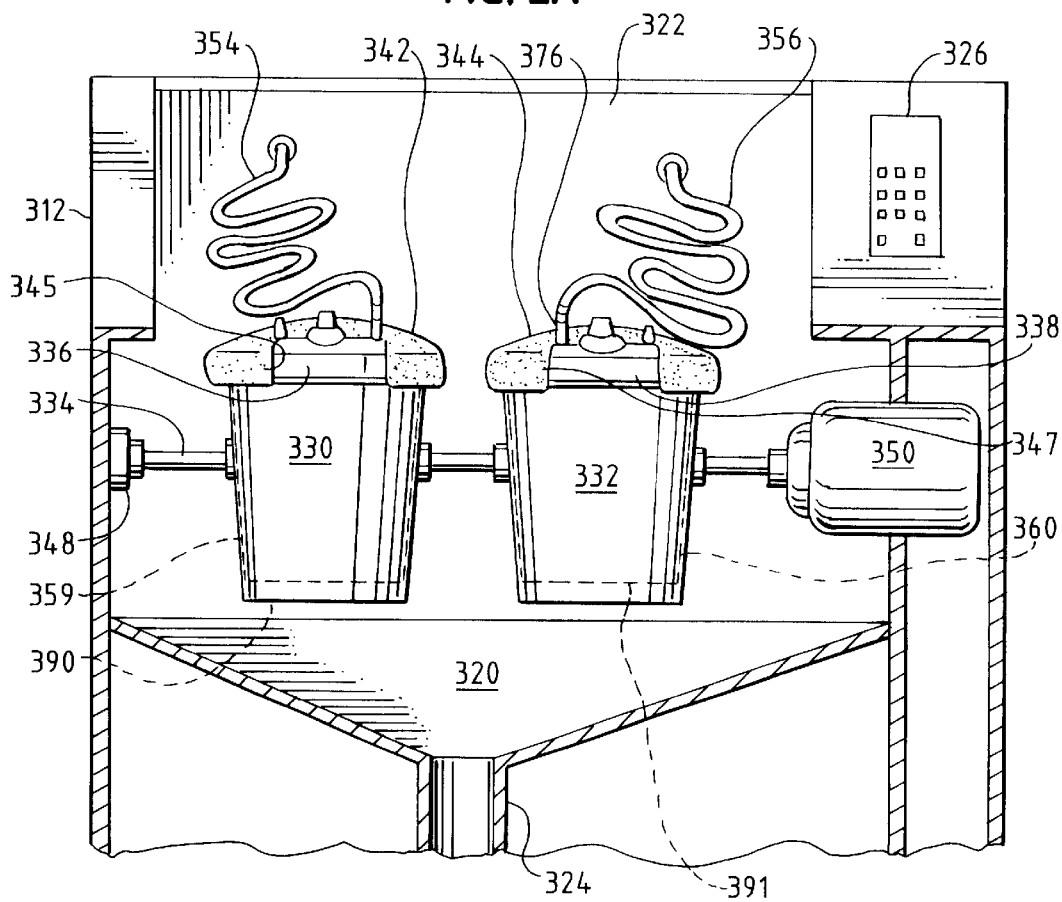

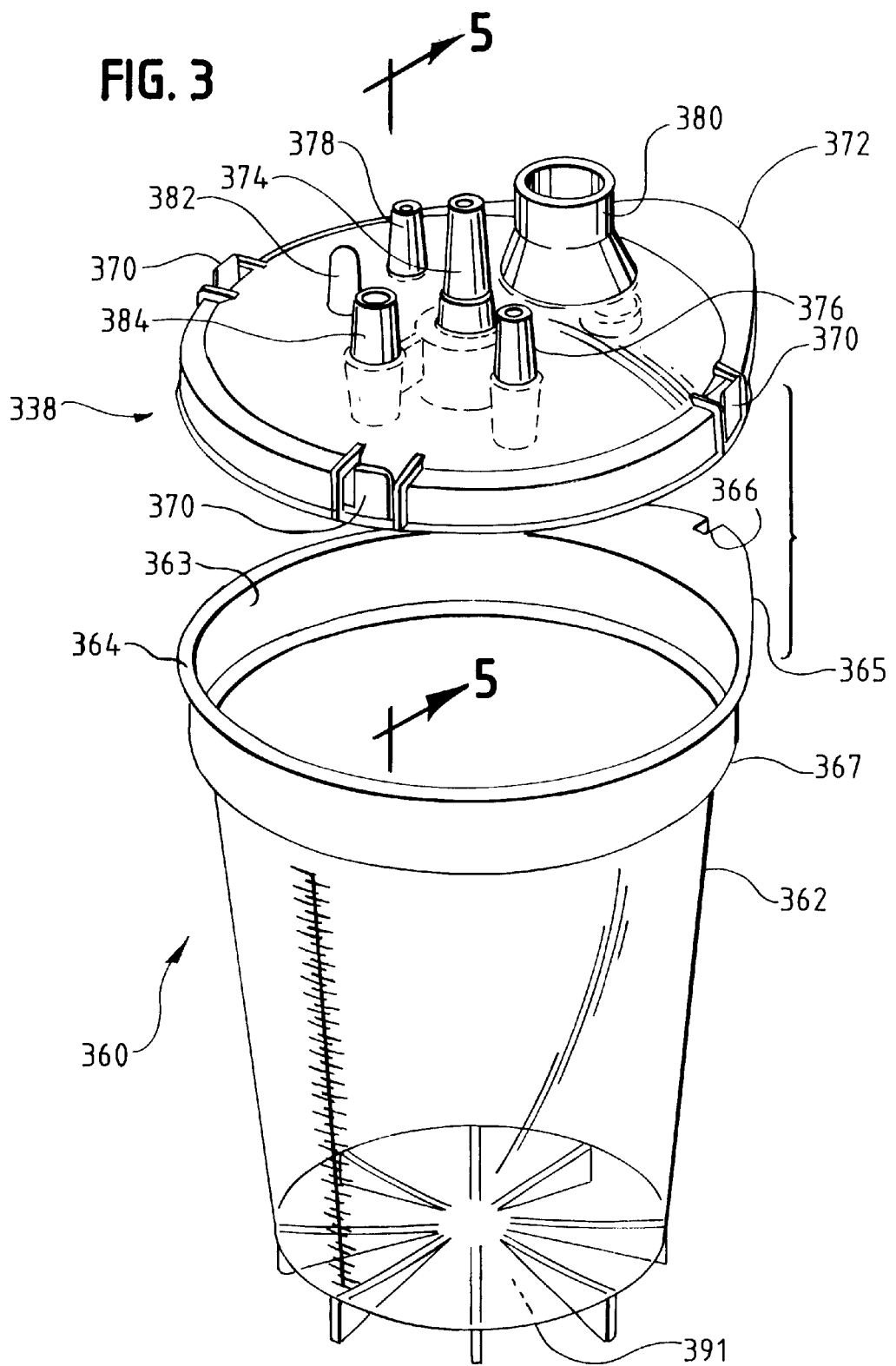

LIQUID WASTE DISPOSAL AND CANISTER FLUSHING SYSTEM AND METHOD

Background of the Invention

I. Field of the Invention

The present invention relates generally to liquid waste disposal and canister flushing, and in particular to the disposal of liquid medical waste from containers which are flushed in preparation for reuse.

II. Description of the Related Art

Various forms of liquid waste are commonly encountered in a variety of different situations. For example, liquid medical wastes are commonly produced in surgery and other medical procedures. Such wastes can include blood and other body fluids of patients, and major surgery can produce a number of containers of such waste from a single patient. Liquid medical waste generates significant disposal problems due to its possible contamination with various infectious diseases, including AIDS, hepatitis, MRSA and tuberculosis. In an effort to combat the risks associated with handling such liquid medical wastes and to protect medical personnel from the spread of infectious diseases, disposal procedures have become increasingly complicated and expensive.

One type of disposal procedure for liquid medical wastes involves emptying the waste canisters from surgery into specially designed plumbing fixtures. However, this procedure can involve risks associated with splash back and aerosolization whereby medical personnel can be exposed to the waste and bacteria present therein.

Another type of procedure involves the centralized collection of the waste with specially designed equipment having a liquid waste reservoir that must periodically be dumped. Such equipment is generally relatively expensive and can add significantly to the cost of equipping a hospital operating room or other treatment facility.

Yet another method of disposing of liquid medical waste involves mixing it with a solidifying agent in the container. The medical waste in the container then disposed of pursuant to regulations governing the disposal of bio-hazardous waste. The disadvantages with this disposal method include the cost of the canister, which becomes a single-use item, and the extra charges for disposing of biohazardous waste, which is sometimes referred to as "red bag" waste.

Liquid medical waste disposal procedures can come under rules and regulations imposed by various governmental and regulatory agencies, including the Occupational Safety and Health Administration (OSHA), the Food and Drug Administration (FDA), the Center for Disease Control (CDC) and the Department of Transportation (DOT).

Heretofore there has not been available a liquid medical waste disposal system and method with the advantages and features of the present invention.

SUMMARY OF THE INVENTION

A liquid waste disposal and canister flushing system for a canister having a lid with a number of ports, including accessory, tandem, patient and vacuum ports, features a cabinet having an opening with a hinged lid. A sink is positioned within the cabinet and communicates with a drain. A canister holder is positioned in the chamber between the sink and the cabinet opening and is supported by a rotating device that rotates the canister holder, and therefore the canister, between initial and drainage positions. In one embodiment of the system, the canister holder takes the form of a bucket sized to removably receive the canister. A lid secures the canister within the bucket. The rotating device includes a rod connected to the bucket. The rod is rotatably mounted within the cabinet and is actuated by an electric motor or lever.

Tubing in communication with sources of pressurized cleaning solution (such as bleach and defoamer) and water is connected to one of the lid ports (other than the accessory port). The canister is rotated into the drainage position and the sources of pressurized cleaning solution and water are activated so that the canister is flushed and its contents draining through the accessory port and into the sink and drain. The lid port to which the tubing is connected may optionally feature a nozzle oriented at an angle so that a swirling action is induced upon pressurized liquid entering the canister to assist in the flushing of residue from the canister.

OBJECTS AND ADVANTAGES OF THE INVENTION

The principal objects and advantages of the present invention include: providing a liquid waste disposal and canister flushing system; providing such a system which facilitates the relatively inexpensive disposal of medical waste; providing such a system which facilitates reuse of medical waste containers; providing such a system which is relatively easily adapted for use with existing medical waste containers; providing such a system which reduces the splashing of medical waste being disposed; providing such a system which can reduce the hazards associated with handling and disposing of medical waste; providing such a system which facilitates the discharge of medical waste into a sewer system; providing such a system which can reduce the amount of disposable components associated with medical waste disposal; providing such a system which provides effective neutralization of various bacteria and infection sources; providing such a system which is usable by medical personnel with relatively little training; providing such a system with a control system which is at least partially automated; providing such a system which is relatively portable; providing such a system which is relatively compact; providing such a system which can be installed with relatively simple plumbing and electrical connections; providing such a system which is economical to manufacture and use, efficient in operation, capable of a long operating life and generally well adapted for the proposed usage thereof; providing a liquid medical waste disposal and canister flushing method; providing such a method which is relatively efficient; providing such a method which is relatively safe; providing such a method which is relatively economical and providing such a method which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a partially broken-away perspective view of an embodiment of the liquid medical waste disposal and canister flushing system of the present invention.

FIGS. 2A and 2B are fragmented sectional views of the liquid medical waste disposal and canister flushing system of FIG. 1 taken along line 2—2 illustrating the initial and drainage positions of the canisters, respectively.

FIG. 3 is an exploded perspective view of a medical canister and lid suitable for use with the present invention.

DETAILED DESCRIPTION OF THE INVENTION

Figure 2B:
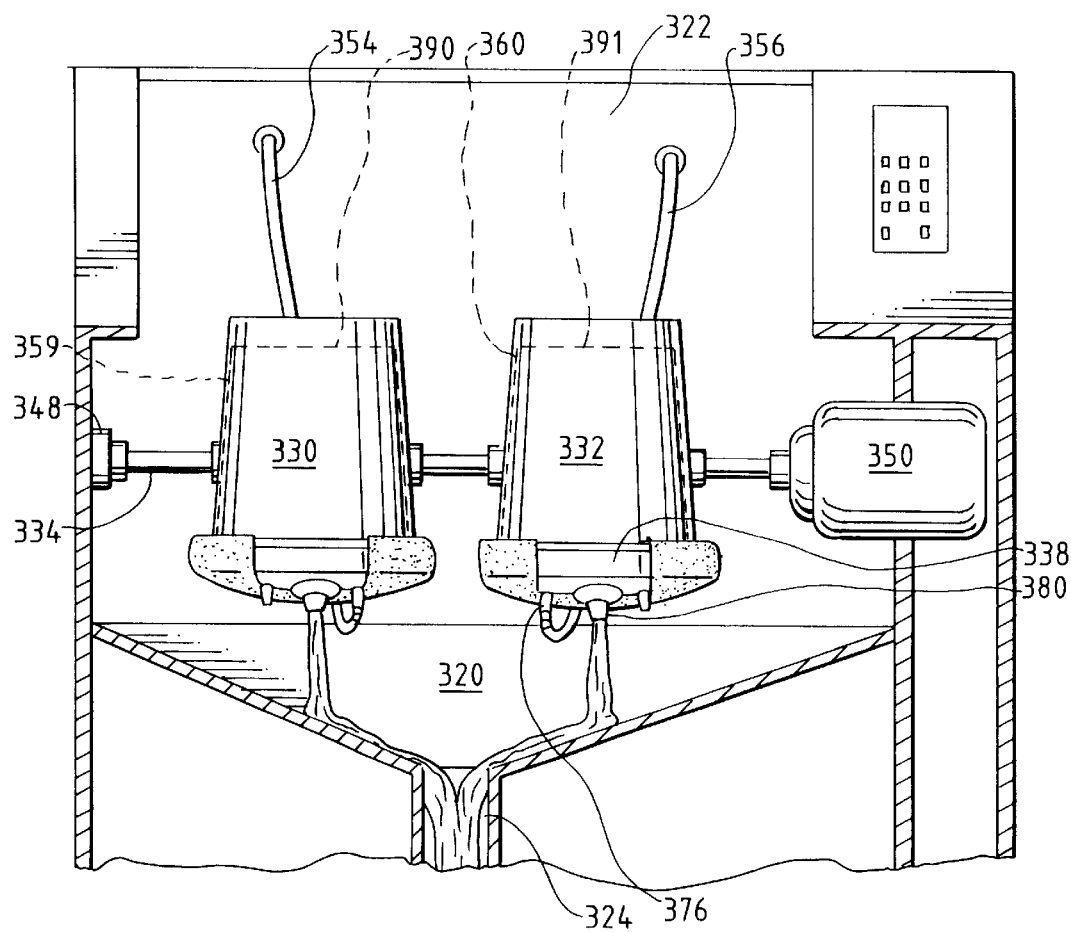

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

An embodiment of the system of the present invention is indicated in general at 310 in FIG. 1. The embodiment of FIG. 1 allows a standard medical canister to be used. A cabinet 312 features an opening 314 that may be covered by a hinged lid 316. A sink 320 is housed within the cabinet so that a chamber 322, which may be accessed through opening 314, is defined. The sink communicates with a drain 324 which leads to a plumbing system so that waste disposed in the sink is carried out of the hospital. As described in commonly-assigned U.S. Pat. No. 5,901,717, drain 324 may optionally communicate with a holding tank for treating the waste before it leaves the hospital. A control panel 326 is positioned upon the cabinet for ease of access by the system operator.

A pair of canister holders in the form of buckets 330 and 332 are supported within chamber 322 by a rod 334. A pair of canisters, illustrated in phantom at 359 and 360 in FIG. 2A and having lids 336 and 338, are removably positioned within the buckets. A pair of bucket lids 342 and 344 removably engage the buckets so that the canisters may be secured in position, as illustrated. The bucket lids feature openings 345 and 347, respectively, so that the ports of canister lids 336 and 338 are accommodated. It should be noted that alternative components, such as straps or clamps, may be utilized to secure the canisters within the buckets. As illustrated in FIG. 2A, rod 334 is rotatably connected to cabinet 312 by a bearing 348 and an electric motor 350. As a result, the buckets, and therefore the canisters positioned therein, may be rotated between an initial position, illustrated in FIG. 2A and a drainage position, illustrated in FIG. 2B. As will be explained in greater detail, pressurized and diluted cleaning solution is supplied to the canisters via flexible tubing 354 and 356, which are constructed from rubber or plastic. It should be noted that while the embodiment illustrated uses two buckets, and therefore accommodates two canisters, the system of the present invention may accommodate an alternative number of canisters (for example one or three).

An example of a canister suitable for use in the system of FIG. 1 is indicated in general at 360 in FIG. 3. Such canisters are typically used in surgery for collecting medical waste including blood and other fluids. The canister 360 includes a body portion 362 with a truncated, generally frustitconical shape. The canister has an open top 363 surrounded by a rim 364, a portion of which extends outwardly to form a flange 365 with a centering slot 366 formed therein. The body portion 362 tapers sharply inwardly from a ledge 367 so that the ledge may rest upon the top of the buckets 330 and 332, as illustrated in FIGS. 1 and 2A. The canister may be molded from polycarbonate plastic, which is reusable and autoclavable up to 220° F., or other materials such as Radel plastic, which is autoclavable up to 321° F.

The detail of lid 338 is also illustrated in FIG. 3. A number of resilient clips 370 are integrally molded into the container lid. As the canister lid 338 is lowered into position atop the canister 360, the tabs snap under the rim 364 to securely hold the lid in place. The lid also features an extended portion 372 that houses a rigid tab (see 373 in FIG. 8) which engages the notch 366 of the canister flange 365 to ensure proper alignment between the cap and canister. A vacuum supply port 374, patient port 376, tandem port 378, accessory port 380, a tube plug 382 and an ortho port 384 are all integrally molded into the container lid. The lid may be molded from, for example, polystyrene plastic.

Figure 4:
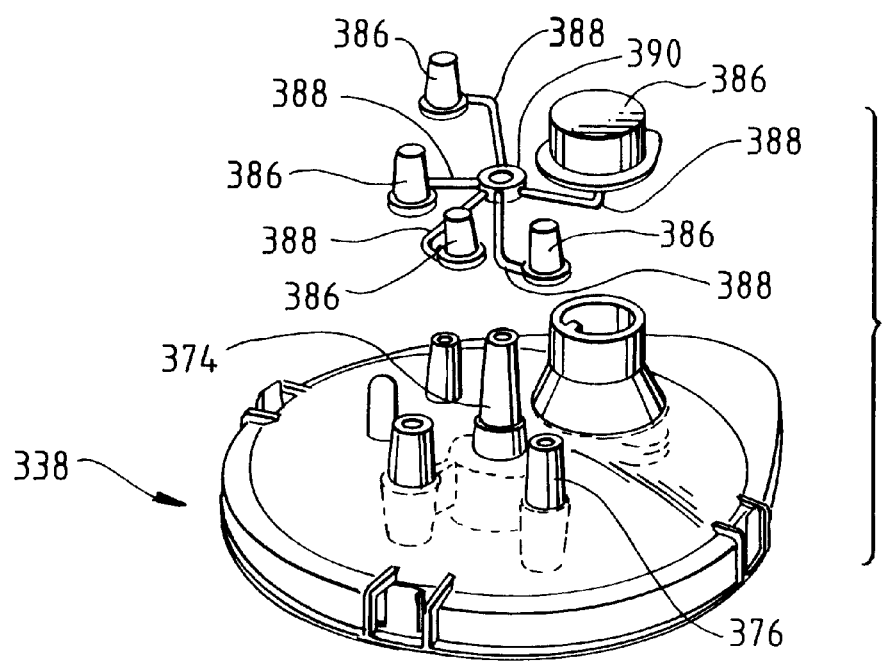
FIG. 4 is an exploded perspective view of the lid of FIG. 3 and caps for the lid ports interconnected in a spider-like arrangement.

As illustrated in FIG. 4, a number of port covering caps 386 are attached by plastic tethers 388 in a spider-like fashion to a center ring 390. The ring is preferably sized to slide over the vacuum port 374 so that the caps may be used to cover all of the lid ports.

During a surgical procedure, the canister is typically configured with the ring 390 positioned upon the vacuum port and the accessory, tandem and ortho ports capped. A tube is connected between the vacuum port and a vacuum source. A second tube is connected to the patient port at one end while the other end is utilized by the surgeon or nurse to withdraw blood and fluids from the patient. When the surgical procedure is completed, or the canister is full, the tubing is disconnected from the vacuum and patient ports. The vacuum and patient ports are then capped so that the canister may be transported and inserted into one of the buckets 330 or 332 of the flushing system as illustrated in FIG. 2A. A lid 342 or 344 may then be used to secure the canister in position.

Figure 5:
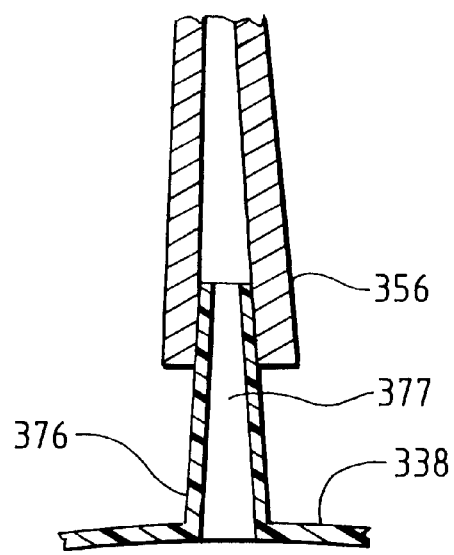
FIG. 5 is an enlarged, fragmented sectional view of a port on the canister lid of FIGS. 3 and 4 taken along line 5—5 of FIG. 3 with tubing positioned thereon so that cleaning solution may be sprayed into the canister.

Once the canister is secured within one of the buckets, the accessory port cap and the cap of another port are removed. Flexible tubing 354 and 356 carries pressurized cleaning solution for flushing the canisters. As illustrated in FIG. 5 for the canister in bucket 332 (FIGS. 2A and 2B), the free end of tubing 356 is placed over the patient port 376. The tubing is sized so that a seal is formed about the patient port 376 so that the pressurized cleaning solution may flow through passage 377 and into the canister. As illustrated in FIGS. 2A and 2B with the canister in bucket 330, the tubing may alternatively be placed over the tandem port or another port (other than the accessory port). It should be noted that all of the lid ports may be uncapped and the ring 390 (FIG. 4) to which the caps are tethered removed from the vacuum port prior to the attachment of tubing 354 and 356.

With the canisters secured within the buckets, the accessory ports uncapped and the tubing connected to ports other than the accessory ports, the cabinet lid 316 (FIG. 1) may be closed. This allows the drainage and flushing cycles to commence when the operator pushes the "start" button on the control panel 326. When the "start" button is pushed, electric motor 350 is energized so that rod 334 and the canisters in buckets 330 and 332 are rotated 180° from the initial position illustrated in FIG. 2A to the drainage position illustrated in FIG. 2B. Alternatively, closing the cabinet lid may automatically activate the electric motor 350 so that the canisters are rotated into the drainage position. Either way, as illustrated in FIG. 2B, blood and other fluids drain out of the canisters through their accessory ports, into the sink 320 and down drain 324. Drain 324 is sized larger than the combined accessory ports of the canisters so that medical waste does not back up in sink 320.

A timed delay of the commencement of the flush cycle is provided after the canisters are rotated into the drainage position illustrated in FIG. 2B. This delay permits substantially complete drainage of the liquid in the canisters before the flush cycle commences. This delay may be accomplished through either an automated control system or manually via separate buttons for rotating the canisters and commencing the flushing cycle. In the case of the latter, the operator may merely wait for the canisters to drain before pushing the button to commence the flushing cycle.

Commencement of the flushing cycle causes the pressurized cleaning solution to enter the canisters via tubing 354 and 356. The entering cleaning solution strikes the now inverted bases of the canisters, illustrated at 390 and 391 in FIGS. 2A, 2B and 3, is directed 360° and cascades down their sides and out of their accessory ports. As a result, the contents remaining in the canisters after drainage is disinfected and flushed down the drain 324.

As a general guideline, it is desirable to flush the canisters with a volume of solution equal to approximately 3 to 4 times their capacities. The cleaning solution mixture preferably comprises water and a suitable agent for killing virus and bacteria. For example, sodium hypochlorite (i.e., bleach) in a solution of about 1200 to 1400 parts per million with water has generally been found to be suitable. A delay of approximately 8 seconds has been found to be sufficient to drain the canisters, and a flush cycle of approximately 45 seconds has generally been found to be sufficient.

Upon completion of the flushing cycle, the flow of diluted cleaning solution is stopped and the canisters are rotated back to the position illustrated in FIG. 2A. The cabinet lid may then be lifted, tubing 354 and 356 disconnected and the canisters removed from the buckets 330 and 332. The canister lids may then be disposed of and the canisters themselves may be reused at a fraction of the cost of disposing of complete canisters full of medical waste.

The solution mixture is preferably chosen to meet the particular objectives of a disposal and flushing system. For example, disinfection and flushing are generally the primary objectives with liquid medical waste containers, which for most reuse purposes do not have to be cleaned to the point where they would be considered sterile, since sterility is normally not required for liquid medical waste canisters. The lids would generally be considered "white" trash in medical facilities due to relatively low concentrations of liquid medical waste thereon and thus would not be subjected to the more stringent requirements typically in place for handling and disposing of the actual liquid medical wastes.

The flushed liquid medical waste from drain 324 mixes with the effluent from the medical facility in its plumbing drainage system and is normally discharged into a municipal sewer system at levels well below the maximums permitted for medical waste effluents.

Figure 6:
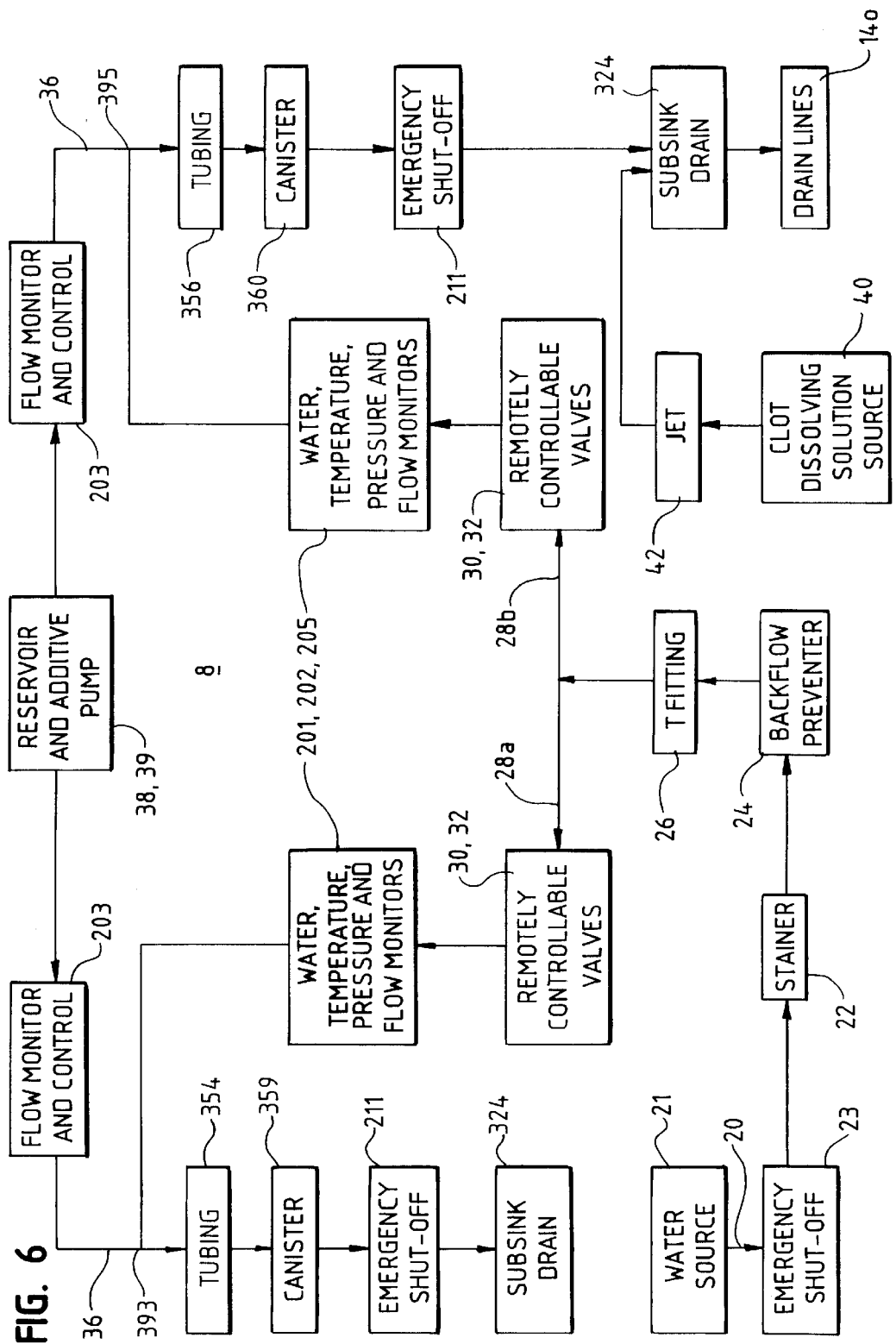
FIG. 6 is a schematic diagram of the plumbing system for the system of FIG. 1.

The system of FIG. 1 is illustrated schematically in FIG. 6. The plumbing system 8 generally includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom. The water inlet line 20 connects to a T-fitting 26, forming first and second supply branches 28a,b.

Each supply subsystem branch 28a,b includes a gate-type shut-off valve 30 and a solenoidactuated valve 32 in line therewith. Each water inlet line 20 ultimately communicates with junctions 393 and 395 that communicate via cleaning solution injection lines 36 with an additive pump and reservoir 38, 39 that are housed within cabinet 312. The reservoir preferably contains a cleaning solution for killing virus and bacteria (for example bleach) and a defoamer. Activation of the pump causes the additives from the reservoir to mix with the water in the plumbing system so that a pressurized and diluted cleaning solution is emitted from tubing 354 and 356.

An optional clot-dissolving solution source 40 communicates with a drain jet 42 directed into the subsink drain 324 and functions to dissolve blood clots therein.

A water flow sensor 202 and an additive flow sensors 203 monitor fluid flow to allow titration of the additive and flow of water to be monitored to calculate concentration of additive (cleaning solution) in the water. As described in commonly-assigned U.S. Pat. No. 5,901,717, a microprocessor may control valves 32 and the pump 39 to achieve the desired additive concentration. Monitoring of water flow by the microprocessor insures compliance with government regulations. A water temperature monitor 205 allows the microprocessor to monitor water temperature. A remotely controlled emergency shut-off 23 and 211 allows the microprocessor to shut off the drain 324 as well as all fluid inputs in the event that monitored parameters are outside of predetermined limits.

Figure 7:
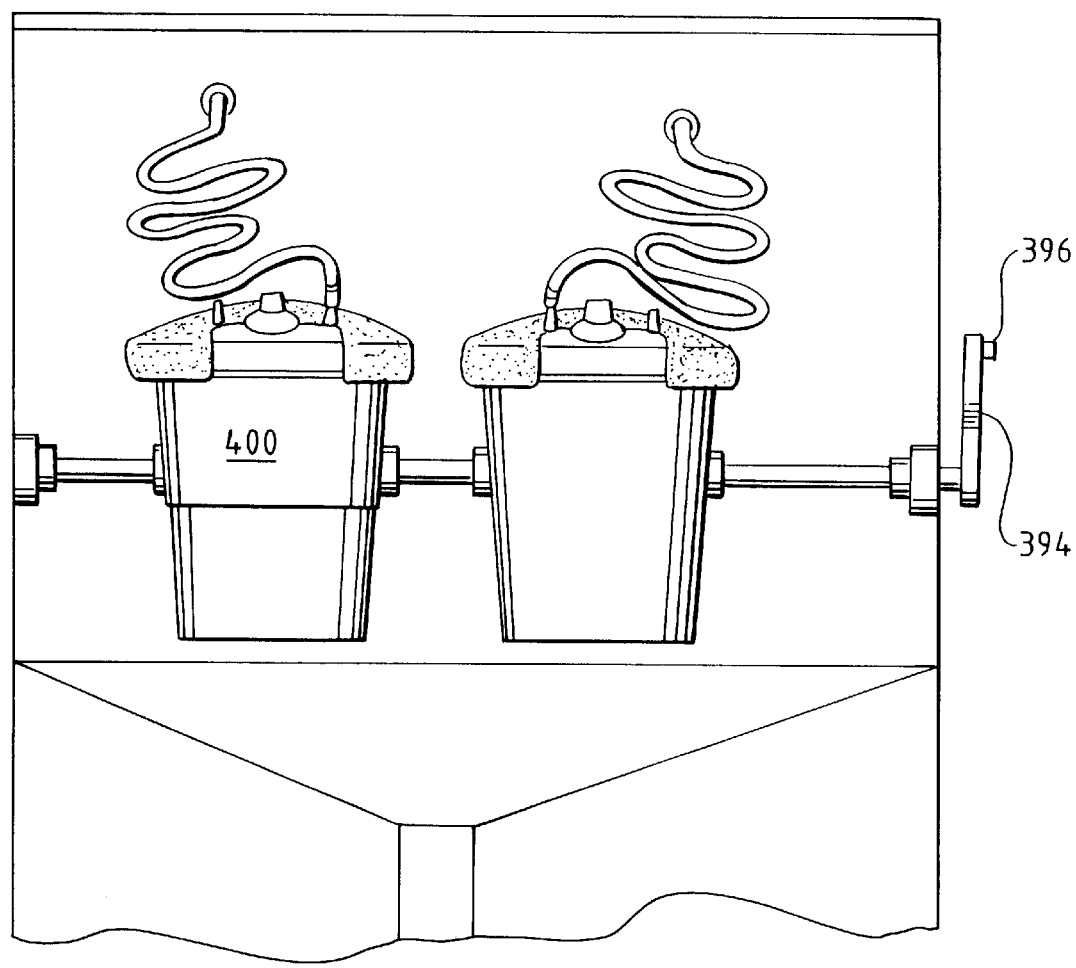
FIG. 7 is a fragmented sectional view corresponding to the view of FIG. 2A illustrating a second embodiment of the liquid medical waste disposal and canister flushing system of the present invention.

An alternative embodiment of the system of present invention is illustrated in FIG. 7. The system of FIG. 7 is identical to the system of FIGS. 1–6 except that the electric motor 350 (FIGS. 2A and 2B) has been replaced by a lever 394. As a result, when the operator of the system of FIG. 7 wishes to rotate the canisters into the drainage position, lever 394 is actuated. Lever 394 preferably includes a locking switch 396 so that the canisters may be secured in the initial position illustrated in FIG. 7 or the drainage position (FIG. 2B). In addition, as illustrated in FIG. 7, a ring 400 may be substituted for a bucket as a canister holder. Canister holders other than buckets or rings may alternatively be used for securing the canisters in the system. Such devices may include, for example, clamps or the like.

Figure 8:
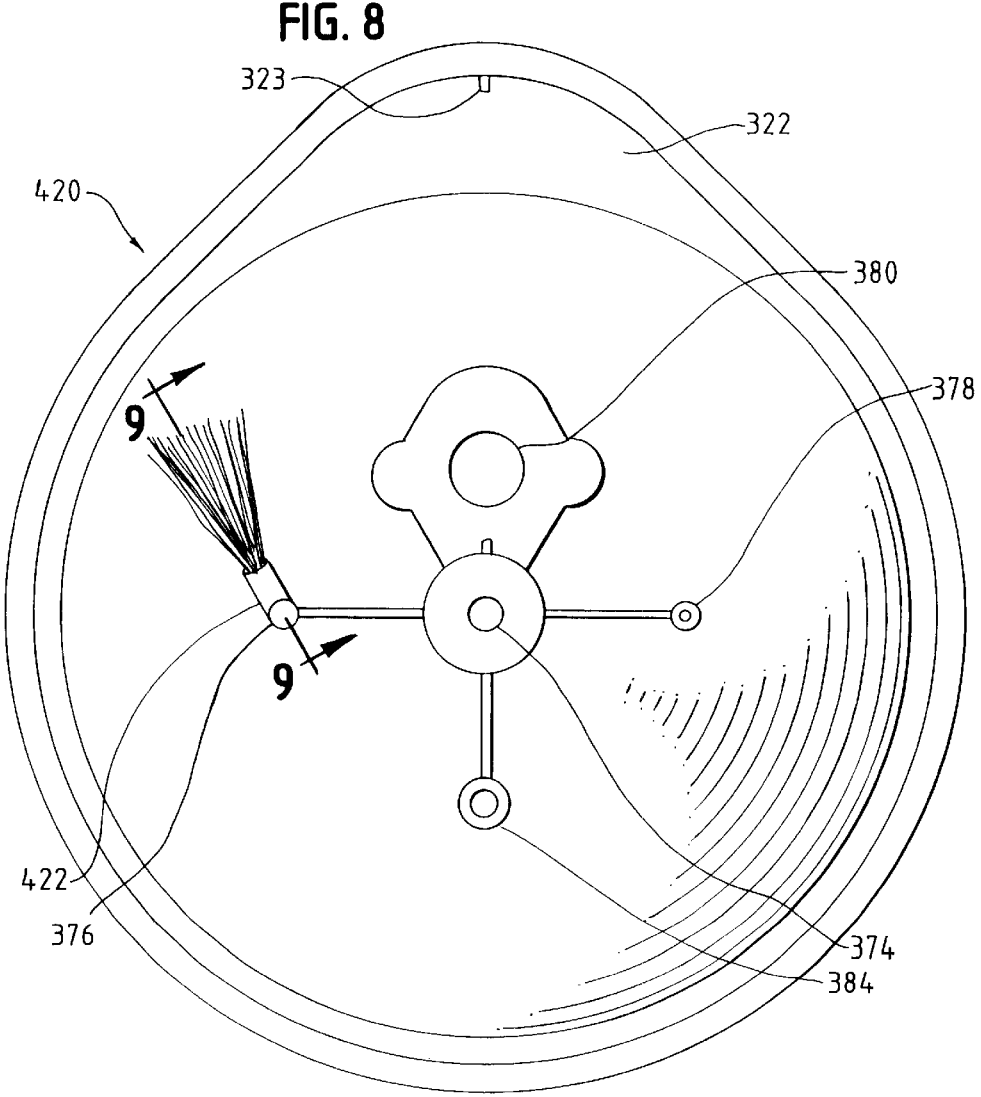
FIG. 8 is a bottom plan view of an alternative embodiment of the lid for the canister of FIGS. 1–3 and 7.

The underside of an alternative embodiment of a canister lid suitable for use with the present invention is illustrated in general at 420 in FIG. 8. With the exception of the construction of port 376, the lid is identical in construction to the lid FIGS. 2A–4. Accordingly, the lid 420 includes an extended portion 372 that houses a rigid tab 373. Furthermore, the lid includes a vacuum supply port 374, patient port 376, tandem port 378, accessory port 380 and an ortho port 384.

Figure 9:
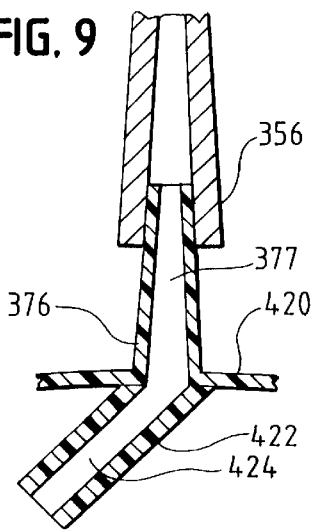
FIG. 9 is an enlarged, fragmented sectional view of a port on the canister lid of FIG. 8 taken along line 9—9 with tubing positioned thereon so that cleaning solution may be sprayed into the canister.

As illustrated in FIGS. 8 and 9, however, the patient port 376 is equipped with a nozzle 422 so as to perform as a special cleaning port. The nozzle may be either integrally molded with the lid 420 or constructed as a separate piece that is attached to the underside of the lid. The nozzle 422 features a passage 424 (FIG. 9) that is in communication with the passage 377 of port 376 and is angled so that cleaning solution flowing therefrom is directed towards the canister interior wall. As a result, a swirling and flushing action is created within the canister during the flushing cycle. It is to be noted that ports 374, 378 or 384 could alternatively be equipped with the nozzle. In addition, the lid alternatively could include a dedicated cleaning port which would be equipped with the nozzle and used solely for flushing purposes.

It should be noted that while a rotating rod connected to an electric motor or lever is illustrated, the present invention encompasses alternative arrangements for rotating the canisters. Such arrangements could include a rail system, for example.

It is to be understood that while certain forms of the present invention have been illustrated and described herein, it is not to be limited to the specific forms or arrangement of parts described and shown.

What is claimed is:

1. A liquid waste disposal and canister flushing system for a canister having a base and a lid with first and second ports comprising:
   a) a cabinet having an opening;
   b) a sink disposed within said cabinet so that a chamber is defined between said sink and the opening in the cabinet;
   c) a drain in communication with said sink;
   d) a canister holder positioned within said chamber, said canister holder adapted to removably receive the canister;
   e) a device for rotating said canister holder so that a canister positioned therein is rotated between an initial position and a drainage position; and
   f) tubing in communication with a source of pressurized liquid, said tubing adapted to engage the first port of the canister lid so that the pressurized liquid can be introduced into the canister to flush residue out through the second port and into the sink and drain when the canister is in the drainage position.

2. The system of claim 1 further comprising a removable lid for covering the cabinet opening.

3. The system of claim 1 wherein said source of pressurized liquid includes a source of pressurized cleaning solution.

4. The system of claim 3 wherein the cleaning solution includes bleach.

5. The system of claim 4 wherein the cleaning solution includes a defoamer.

6. The system of claim 1 wherein the canister holder includes a bucket sized to removably receive the canister.

7. The system of claim 1 wherein the canister holder includes a ring sized to removably receive the canister.

8. The system of claim 1 wherein the device for rotating said canister holder includes a rod connected to the canister holder, said rod rotatably mounted within said cabinet, and an apparatus for rotating said rod.

9. The system of claim 8 wherein the apparatus for rotating said rod includes an electric motor.

10. The system of claim 8 wherein the apparatus for rotating said rod includes a lever.

11. The system of claim 1 further comprising a nozzle adapted to be placed in communication with the first port of the canister lid, said nozzle oriented at an angle so that a swirling action is induced upon the pressurized liquid entering the canister to assist in the flushing of residue from the canister.

12. A liquid waste disposal and canister flushing system comprising:
   a) a canister including a lid with first and second ports;
   b) a cabinet;
   c) a sink positioned within said cabinet, said sink in communication with a drain;
   d) a canister holder removably securing the canister above said sink;
   e) a device for rotating the canister holder, and therefore said canister, between initial and drainage positions; and
   f) tubing in communication between the first port of the canister lid and a source of pressurized liquid, said source of pressurized liquid activated when said canister is in the drainage position so that the canister is flushed with its contents passing through the second port of the canister lid, into the sink and down the drain.

13. The system of claim 12 wherein the pressurized liquid is a cleaning solution.

14. The system of claim 12 wherein the canister holder includes a bucket sized to removably receive the canister.

15. The system of claim 12 wherein the canister holder includes a ring sized to removably receive the canister.

16. The system of claim 12 wherein the device for rotating said canister holder includes a rod connected to the canister holder, said rod rotatably mounted within said cabinet, and an apparatus for rotating said rod.

17. The system of claim 16 wherein the apparatus for rotating said rod includes an electric motor.

18. The system of claim 16 wherein the apparatus for rotating said rod includes a lever.

19. The system of claim 12 further comprising a nozzle in communication with the first port of the canister lid, said nozzle oriented at an angle so that a swirling action is induced upon pressurized liquid entering the canister to assist in the flushing of residue from the canister.

20. A method of disposing of liquid waste from a canister having a lid with first and second ports comprising the steps of:
   a) providing a sink and a drain;
   b) providing a source of pressurized liquid;
   c) connecting the first port of the canister lid to the source of pressurized liquid;
   d) rotating the canister above the sink into a drainage position;
   e) flushing the canister with the source of pressurized liquid; and
   f) draining the liquid waste in the canister out of the second port and into the sink and drain.

* * * * *